United States Patent [19]

Lang et al.

[11] Patent Number: 4,860,737
[45] Date of Patent: Aug. 29, 1989

[54] WOUND DRESSING, MANUFACTURE AND USE

[75] Inventors: Stephen M. Lang, Wicken Benhunt, Nr. Saffron Walden; David F. Webster, Bishops Stortford, both of United Kingdom

[73] Assignee: Smith and Nephew Associated Companies p.l.c., United Kingdom

[21] Appl. No.: 522,414

[22] Filed: Aug. 11, 1983

Related U.S. Application Data

[63] Continuation-in-part of Ser. No. 516,119, Jul. 20, 1983, which is a continuation-in-part of Ser. No. 506,501, Jun. 21, 1983, which is a continuation-in-part of Ser. No. 396,754, Jul. 9, 1982, which is a continuation-in-part of Ser. No. 396,732, Jul. 9, 1982, which is a continuation-in-part of Ser. No. 345,550, Feb. 3, 1982, which is a continuation-in-part of Ser. No. 345,488, Feb. 3, 1982.

[30] Foreign Application Priority Data

| Feb. 13, 1981 | [GB] | United Kingdom | 8104568 |
| May 22, 1981 | [GB] | United Kingdom | 8115742 |
| Feb. 12, 1982 | [GB] | United Kingdom | 8204133 |
| Feb. 12, 1982 | [GB] | United Kingdom | 8204132 |
| Jun. 22, 1982 | [GB] | United Kingdom | 8218088 |
| Jul. 21, 1982 | [GB] | United Kingdom | 8221112 |
| Aug. 12, 1982 | [GB] | United Kingdom | 8223253 |

[51] Int. Cl.$^4$ .............................................. A61F 13/00
[52] U.S. Cl. ..................................... 128/156; 604/369
[58] Field of Search ................ 128/155, 156; 604/369, 604/366, 370

[56] References Cited

U.S. PATENT DOCUMENTS

| 3,888,248 | 6/1975 | Moore et al. | 604/369 |
| 3,927,669 | 12/1975 | Glatt | 128/156 |
| 4,146,027 | 3/1979 | Hoey | 128/156 |
| 4,203,435 | 5/1980 | Krull et al. | 128/156 |
| 4,231,357 | 11/1980 | Hessner | 128/156 |
| 4,340,043 | 7/1982 | Seymour | 128/132 D |

Primary Examiner—C. Fred Rosenbaum
Attorney, Agent, or Firm—Jacobs & Jacobs

[57] ABSTRACT

A low adherency wound dressing which comprises a wound facing layer, an intermediate absorbent layer and an outer layer wherein the wound facing layer comprises a conformable net of elastomer, the intermediate absorbent layer comprises a conformable open cell foam of hydrophilic polymer, and the outer layer comprises a conformable microporous film; and a process for making said dressing.

11 Claims, No Drawings

WOUND DRESSING, MANUFACTURE AND USE

This is a continuation-in-part of application U.S. Ser. No. 345,488 filed Feb. 3, 1982 entitled "Wound Dressing Manufacture and Use", now abandoned. U.S. Ser. No. 345,550 filed Feb. 3, 1982 entitled "Wound Dressing, Manufacture and Use", abandoned, U.S. Ser. No. 396,732 filed July 9, 1982 entitled "Wound Dressings, Manufacture and Use", now U.S. Pat. No. D280,020, U.S. Ser. No. 396,754 filed July 9, 1982 entitled "Wound Dressings, Manufacture and Use", abandoned, U.S. Ser. No. 506,501 filed June 21, 1983 entitled "Wound Dressing, Manufacture and Use", abandoned, and U.S. Ser. No. 516,119 filed July 20, 1983 entitled "Adhesive Wound Dressing" by Stephen Michael Lang and David Fitzgerald Webster, now abandoned.

Burns and other related wounds such as donor sites and the like present a serious problem in that they tend to produce large amounts of exudate which can cause conventional dressings to become saturated or to stick to the wound or even become infected. One method of covering such wounds has been to cover the wound with a material into which new epithelial or fibroblast growth can penetrate. Dressings of this kind are disclosed in U.S. Pat. Nos. 3,526,224, 3,648,692 and 3,949,742.

However such dressings can be extremely painful to remove and often require surgical excision. A fundamentally different approach requiring a fundamentally different type of dressing is to employ materials that are designed to reduce the propensity to adhere to the wound. Dressings of this kind are disclosed in British Pat. No. 439085, French Pat. No. 947609, U.S. Pat. Nos. 3,543,750, 2,923,298 and British Pat. No. 778813 which later patents cover successfully used materials such as Melolin ("Melolin" is a registered Trade Mark of T. J. Smith and Nephew Limited, Welwyn Garden City, Herts., U.K.). One more recent attempt at non-adherent dressings is U.S. Pat. No. 3,709,221 which discloses a dressing having an outer microporous, liquid repellent fibrous layer, an inner macroporous fibrous layer and an absorbent intermediate layer which was also envisaged as normally being fibrous. In order to reduce the tendency of this material to adhere to the wound the inner layer had to be treated with an agent to render it non-wetted by body liquid. It is now realised that it would be desirable to provide a dressing in which the wound facing layer did not require special treatment. As it will become apparent hereinafter it has now been discovered that by avoiding fibrous materials it is possible to produce a dressing with reduced tendency to adhere to wounds without the need for special treatments. An attempt at producing an absorbent dressing is described in U.S. Pat. No. 3,888,248 which describes a dressing fabricated from at least four sheet materials. The wound facing part of the dressing apparently consists of a grid or scrim coated with polyethylene in such a manner that the polyethylene surrounds the filaments of the grid and collects any loose thread or particle that may be present in the core material. It is now realised that it is desirable to avoid the use of wound facing layers that can allow such penetration of the central layer to the wound surface. It has also been realised that it would be desirable to provide a material that was highly conformable to the wound so that it is possible to minimise the quantity of exudate between the wound surface and the dressing. U.S. Pat. Nos. 3,709,221 and 3,888,248 disclose materials which are bonded along their edges which may reflect a desire to improve conformability. The dressing of the present invention allows for bonding over the whole of the operative area while retaining flexibility.

Accordingly the present invention provides a wound dressing which consists essentially of a low wound adherency wound facing layer, an absorbent layer and optionally an outer layer, characterised in that the wound facing layer comprises a conformable apertured film, the absorbent layer comprises a conformable hydrophilic foam and the outer layer is either absent or is a continuous moisture vapour transmitting conformable film or is a conformable elastically extensible net or is a conformable backing layer which has an adhesive layer on one surface thereof, at least one of said backing layer and said adhesive layer being continuous to provide a barrier to bacteria and to liquid water or is a conformable microporous film.

Accordingly the present invention provides a low adherency wound dressing which comprises a wound facing layer, an intermediate absorbent layer and an outer layer which wound dressing is characterised in that the wound facing layer comprises a conformable net of elastomer, the intermediate absorbent layer comprises a conformable open cell foam of hydrophilic polymer and the outer layer comprises a conformable microporous film.

In one aspect the invention provides a low adherency wound dressing which consists essentially of a wound facing layer which is a conformable net of elastomer, an intermediate absorbent layer and an outer layer as defined above, optionally with a topically effective medicament in the intermediate absorbent layer.

Normally the three layers of the dressing of this invention are attached in a contiguous and co-extensive manner; that is the dressing is normally provides in the form of a laminate.

Materials for use in the dressing of the invention and methods of preparing these materials are disclosed in United Kingdom patent application Nos. 8204132 and 8204133 and their corresponding patent applications: Australian patent application No. 80375, Canadian patent application No. 396191, Danish patent application No. 638/82, European patent application Nos. 307/82, Japanese patent application No. 21948/82, New Zealand patent application No. 199,684, South African patent application No. 820933 and U.S. patent application Ser. Nos. 345,488 and 345,550 the contents of which are incorporated herein by cross reference.

Wound dressings of the invention can suitably have a moisture vapour transmission rate of 300 to 5000 grams and preferably 500 to 2000 grams/square meter/24 hours at 37.5° C. at 100% to 10% relative humidity difference. It has been found that such moisture vapour transmission rates will allow the wound under the dressing to heal under moist conditions without causing the skin surrounding the wound to macerate.

The conformable net of the elastomer dressing of the invention acts as a low adherency wound facing layer. This layer allows wound exudate to pass to the absorbent layer but prevents the absorbent layer making direct contact with the wound surface.

The net used in this invention is preferably an integral net, that is a net with strands and junctions which have been formed integrally during manufacture.

Preferably the net is sufficiently conformable to allow the wound dressing to conform with the body contours and thereby maintain overall contact with the wound surface to ensure that exudate from the wound is absorbed.

It is also desirable that the net should be sufficiently elastically extensible to adjust to any dimensional changes in the absorbent layer.

Suitable nets will have an elongation at break of 100% to 800% desirably 200% to 750% and preferably 300% to 700% when measured as a 2.5 cm wide strip at a 30 cm/minute strain rate at 20° C.

Normally the net of elastomer is made of a pharmaceutically acceptable water insoluble elastomer. Suitable elastomers include polyurethanes, polybutadiene and the like. Preferred polyurethane and polybutadiene elastomers are disclosed in the aforementioned patent applications.

The net of the wound facing layer of the dressing of the invention can have any convenient form depending on the chosen arrangement of strand, junctions and aperture areas and also their shapes and relative size.

Suitable forms of net for the dressings of the invention and the physical characteristics of these nets including preferred numbers and sizes of the net apertures, areas of the voids (apertures), thicknesses and weights of the net are disclosed in the aforementioned patent applications.

The conformable hydrophilic polymer open cell absorbent layer used in dressings of the invention is capable of absorbing wound exudate for example from a burn. It is desirable that the hydrophilic polymer foam layer absorbs the wound exudate rapidly as this enhances the low adherency properties of the absorbent pad. Such rapid absorption prevents undesirable pooling of exudate between the dressing and the wound.

The ability of open cell hydrophilic polymer foam layers to absorb and retain fluids depends to some extent on the size of the foam cells, the porosity of the foam and the thickness of the foam layer. Apt sizes of the foam cells, cell membrane opening areas and thicknesses of the foam are disclosed in the aforementioned patent applications.

The use of such foams of hydrophilic polymer in the absorbent pad of dressings of the invention can allow the wound to be maintained in a moist condition even when the exudate produced has been absorbed and removed from the wound surface.

Favoured hydrophilic polymer foams are hydrophilic polyurethane and especially those which are made of cross-linked hydrophilic polyurethane. Preferred foams can be made by reacting a hydrophilic isocyanate terminated polyether prepolymer with water. Favoured hydrophilic polyurethane foams of this type include those known as Hypol foams. Hypol foams can be made from Hypol hydrophilic prepolymers marketed by W. R. Grace and Co.

The conformable film microporous outer layer of the wound dressing of the invention may be used to regulate the moisture loss from the wound areas under the dressing and also to act as a barrier to bacteria to delay or prevent bacteria on the outside surface of the dressing penetrating to the wound area.

Suitable conformable microporous films will have a moisture vapour transmission rate of 300 to 5000 grams preferably 500 to 4000 grams/square meter/24 hrs at 37.5° C. at 100% to 10% relative humidity difference. It has been found that such moisture vapour transmission rates of the film allow the wound under the dressing to heal under moist conditions without causing the skin surrounding the wound to macerate.

Suitable conformable microporous films have an average pore diameter of less than 2 microns desirably less than 0.6 microns and preferably less than 0.1 microns. Such microporous films should have an average pore diameter of greater than 0.01 microns.

Suitable conformable microporous films have a thickness of 25 to 400 microns preferably 50 to 300 microns. The conformable microporous film will be made of a polymer. Suitable polymers include plasticised polyvinyl chloride elastomers of polyurethane and ethylene vinyl acetate copolymer elastomers.

A favoured conformable microporous film comprises a microporous plasticised polyvinyl chloride film having an average pore diameter of less than 2 microns, a thickness of 250 to 300 microns and a moisture vapour transmission rate of 3000 to 5000 g/m$^2$/24 hours at 37.5° C. at a relative humidity difference of 100% to 10% relative humidity.

The wound dressing of the invention can contain a topically effective medicament. Most suitably the medicament is an antibacterial agent. Preferably the antibacterial agent is a broad spectrum antibacterial agent such as a silver salt for example silver sulphadiazine, an acceptable iodine source such as povidone iodine (also called polyvinyl pyrrolidone iodine or PVP/I), chlorhexidine salts such as the gluconate, acetate, hydrochloride or the like salts or quaternary antibacterial agents such as benzalkonium chloride or the like.

The medicament is preferably located in the foam layer of the dressing.

Preferred amounts of suitable medicaments for incorporation into the foam layer of dressing of the invention are disclosed in the aforementioned patent applications.

The wound dressing of this invention may be in any convenient form of shape or size. In a preferred form the wound dressing is a pad of rectangular shape. In another preferred form the wound dressing can be an elongate strip which may be used as a bandage or may be used to prepare smaller dressings.

It is desirable that the wound dressing of this invention are sterile. The wound dressing of the invention is advantageously provided in bacteria impervious pouches. Such packed forms can be prepared under aseptic conditions or alternatively sterilised after packing by a conventional procedure. A favoured sterilisation procedure is heat sterilisation, for example by steam. Other favoured procedures are ethylene oxide sterilisation or gamma irradiation.

In another aspect the invention provides a process of making a low adherency wound dressing of the invention which comprises bringing together a conformable net of elastomer, an intermediate absorbent layer comprising an open cell foam of hydrophilic polymer and an outer layer comprising a conformable microporous film.

Normally the bringing together of the layers will be a lamination process.

The previously formed individual layers can be formed into a laminate by bonding the layers together in one or more laminating processes. Suitable bonding methods include heat sealing or adhesive bonding providing that the adhesive layer is discontinuous. Such discontinuous adhesive bonding layers will be moisture vapour transmitting and will also allow the passage of wound exudate from the wound facing net layer to the absorbent hydrophilic foam layer when used to bond these layers together.

Preferred discontinuous adhesive bonding layers comprise a pattern of intersecting sets of parallel lines of adhesive for example a diamond pattern which gives adhesive free areas of rectangles, parallelograms and like shapes. Methods of preparing such discontinuous pattern adhesive layers are disclosed in British Pat. No. 819,635. Such patterns can be produced by spraying-on the adhesive. Favoured adhesive bonding compositions include acrylate ester copolymers and polyvinyl ethyl ethers.

A preferred bonding method for forming the film-/foam/net laminate of the invention is heat sealing. The net and film layers can be heat sealed to the foam layer by heat and pressure in a conventional manner in one or more laminating processes. An apt heat sealing process comprises passing the net or film layer in contact with the foam layer through the nip of a heated metal roller and rubber roller under low pressure. To ensure that the net or film is in a heat softened state it is desirable that the net or film layer is adjacent to the heated metal roller. Thus by this process the laminate can be formed in two consecutive operations in which for example the film layer is laminated to the foam layer in a first pass through the laminating rollers and the net layer to the opposed face of the foam in a second pass through the rollers. Alternatively, the laminate can be formed in one operation by passing the layers through the nips of two sets of laminating rollers.

When the net has been formed on an embossed film casting sheet, it is preferred that the net is supported on its embossed film casting sheet during the heat lamination process. It has been found with this arrangement that the supported net has less tendency to be compressed and 'flattened' into the surface of the foam by heat and pressure of laminating process thus ensuring that the net is a discrete layer on the foam surface.

In a continuous process the wound dressing can be made in the form of a continuous strip which is then cut up into suitable sized dressings.

Processes for forming the materials used in the dressings of the invention including the preferred hydrophilic polyurethane foam layers, the preferred polyurethane elastomer net layers, the preferred acrylate ester copolymer and polyvinyl ethyl ether adhesive bonding composition and laminates of these materials are disclosed in the aforementioned patent applications.

Suitable microporous films for the outer layer of a wound dressing of the invention can be made by the method disclosed in British Pat. No. 884,232.

The invention will now be illustrated by the following examples.

Preparation of net

An integral diamond pattern polyurethane net of which 4 apertures/cm was prepared in the same manner as in Example 22 of British patent application No. 8204132 using a melt embossed polypropylene sheet (polypropylene containing 40% by weight chalk filler reference PXC 4999 available from ICI Plastics Limited) instead of a high density polyethylene sheet.

Preparation of the absorbent layer

Using the two component dispensing Vari-o-mix (supplied by Prodef Engineering Limited) a foaming mixture was formed by mixing Hypol F H P 2002 and Brig 72 (1% aqueous solution) in the ratio of 1:2. The foaming mixture was put into the coating head by means of an output nozzle in the form of a 15 cm wide 'fishtail die' and coated onto a silicone coated release paper (Stearalese No. 46 available from Sterling Coated Papers Limited) by means of a knife over roller coating head set at a gap of 1 mm. The cast foam was dried by passage through an air circulating oven at a temperature of 50° C. for 5 minutes. The cast hydrophilic polyurethane foam had a thickness of 2 mm.

Preparation of the film layer

A microporous plasticised polyvinyl chloride film (275 microns thick) having an average pore diameter of less than 2 microns was made by the method disclosed in British Pat. No. 884,232. The film was then coated with discontinuous pattern of a polyvinyl ethyl ether pressure sensitive adhesive solution (adhesive composition A of British Pat. No. 1,280,631) by the method given in British Pat. No. 819,635 and passed into a heated oven to give a dry weight per unit area of 30 g/m$^2$. The discontinuous adhesive coating had diamond pattern of adhesive free areas between intersecting parallel lines of adhesive (4 per cm). The adhesive coated film was laminated to a silicone coated release protector layer (Steralease No. 15 available from Sterling Coated Papers Limited).

Preparation of low adherency wound dressings

The polyurethane net on its embossed casting sheet was heat laminated to the hydrophilic polyurethane foam on its silicone coated release casting paper by passing the layers between the nip of a silicone rubber roller and a steel roller heated by circulating oil to a temperature of 135° C. The embossed sheet carrying the polyurethane net was fed against the heated steel roller to ensure that the net was in a heat softened condition prior to its lamination to the foam.

The silicone coated release paper was then removed from the foam layer of net/foam laminate and the adhesive coated microporous film (with protector removed) was laminated to the foam surface by a similar laminating process in which the steel roller was maintained at room temperature.

The enbossed carrier sheet was then removed from the net surface to give a three layer laminate strip and the strip cut into dressings.

DEMONSTRATION OF EFFECTIVENESS ABSORBENCY TESTING

A dressing formed as described in the Example cut to a size of 5.2 cm×5.2 cm (approximately) was placed under light pressure with the net-carrying surface of the foam in contact with horse serum. The serum was available through an orifice 1 cm in diameter at zero hydrostatic pressure. The penetration of the serum was followed by observation and by weighing the dressing before and at intervals during the absorption process. Initially the rate of absorption was slow but increased rapidly so that, after 30 minutes from the start of the experiment, the pad was observed to be saturated and contained 8 g of serum, as measured by the weight difference between the start and end of the experiment.

The experiment showed that the absorption capacity of the foam was not restricted by the presence of a net on one surface and a film on the other.

DEMONSTRATION OF EFFECTIVENESS MOISTURE VAPOUR PERMEABILITY (MVP) DETERMINATION

Discs of the dressing material that is a laminate of net/foam/adhesive/backing layer, to be tested are clamped over Payne Permeability Cups (flanged metal cups) using sealing rings and screw clamps. The exposed surface of the test sample is 10 cm$^2$. Each cup contains approximately 10 ml of distilled water.

After weighing the cups are placed in a fan assisted electric oven maintained at 37.5°. The relative humidity within the oven is maintained at approximately 10% by placing 1 kg of anhydrous 3–8 mesh calcium chloride on the floor of the oven.

The cups are removed after 24 hours, allowed to cool for 20 minutes and reweighed. The MVP of the test material is calculated from the weight loss and expressed in units of grams of weight per square meter per 24 hours, at 37.5° C. at 100–10% relative humidity difference.

The results were as follows

| 5 samples of | Moisture vapour permeability (g/m$^2$/24 hrs) |
| --- | --- |
| Dressing material (ex Example) | 1616, 1612, 1866, 1720, 1740 |

We claim:

1. A laminate wound dressing which consists essentially of a low adherency wound facing layer, an absorbent layer and an outer layer laminated together wherein the wound facing layer comprises a conformable net of elastomer, the absorbent layer comprises a conformable hydrophilic foam and the outer layer comprises a conformable microporous film which is a barrier to bacteria and liquid water.

2. A wound dressing according to claim 1 which consists essentially of a wound facing layer which is a conformable net of elastomer, an intermediate absorbent layer and an outer layer, both as defined in claim 1, optionally with a topically effective medicament in the intermediate absorbent layer.

3. A wound dressing according to claim 1, wherein the outer layer has a moisture vapour transmission rate of 500 to 4000 grams/square meter/24 hours at 37.5° C. at 100% to 10% relative humidity difference.

4. A wound dressing according to claim 1 wherein the microporous film outer layer has a mean pore diameter of 0.01 to 2 microns.

5. A wound dressing according to claim 1 wherein the microporous film outer layer has a thickness of 50 to 300 microns.

6. A wound dressing according to claim 1 wherein the outer layer is a microporous plasticised polyvinyl chloride film having an average pore diameter of 0.01 to 2 microns, a thickness of 250 to 300 microns and a moisture vapour transmission rate of 300 to 5000 g/m$^2$/24 hours at 37.5° C. at a relative humidity difference of 100% to 10% relative humidity.

7. A wound dressing according to claim 6, wherein the average pore diameter is 0.01 to 0.1 microns.

8. A wound dressing according to claim 6, wherein the intermediate absorbent layer is a cross-linked hydrophilic polyurethane foam made by reacting a hydrophilic isocyanate terminated polyether prepolymer with water, and optionally contains a topically effective medicament.

9. A wound dressing according to claim 6, wherein the wound facing layer is an integral net.

10. A wound dressing according to claim 1 wherein the wound facing layer is made of polyurethane.

11. A wound dressing according to claim 1 wherein the outer layer is microporous polyvinylchloride.

* * * * *